US008758422B2

(12) United States Patent  
Vrba

(10) Patent No.: US 8,758,422 B2  
(45) Date of Patent: Jun. 24, 2014

(54) EDGE PROTECTION VIA TAPERED BALLOON WRAP

(75) Inventor: Anthony C. Vrba, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1155 days.

(21) Appl. No.: 12/136,973

(22) Filed: Jun. 11, 2008

(65) Prior Publication Data

US 2009/0312828 A1  Dec. 17, 2009

(51) Int. Cl.  
*A61F 2/06* (2013.01)

(52) U.S. Cl.  
USPC .......................................... 623/1.11; 606/194

(58) Field of Classification Search  
CPC ... A61F 2/958; A61M 25/1002; A61M 25/10; A51M 2025/1004; A51M 2025/1086  
USPC ......... 623/1.11; 606/191, 192, 194, 198, 200; 604/96.01, 103.06–103.09, 916  
See application file for complete search history.

(56) References Cited

U.S. PATENT DOCUMENTS

| | | | |
|---|---|---|---|
| 4,881,547 A | 11/1989 | Danforth | |
| 4,917,088 A | 4/1990 | Crittenden | |
| 5,037,392 A | 8/1991 | Hillstead | |
| 5,053,007 A | 10/1991 | Euteneuer | |
| 5,104,376 A | 4/1992 | Crittenden | |
| 5,141,494 A | 8/1992 | Danforth et al. | |
| 5,147,302 A | 9/1992 | Euteneuer et al. | |
| 5,226,887 A | 7/1993 | Farr et al. | |
| 5,334,146 A | 8/1994 | Ozasa | |
| 5,342,307 A | 8/1994 | Euteneuer et al. | |
| 5,484,385 A * | 1/1996 | Rishton ........................... 600/16 |
| 5,649,908 A | 7/1997 | Itoh | |
| 5,792,415 A | 8/1998 | Hijlkema | |
| 5,853,389 A | 12/1998 | Hijlkema | |
| 6,033,380 A * | 3/2000 | Butaric et al. ........... 604/103.07 |
| 6,129,737 A | 10/2000 | Hamilton et al. | |
| 6,296,655 B1 | 10/2001 | Gaudoin et al. | |
| 6,348,065 B1 | 2/2002 | Brown et al. | |
| 6,491,711 B1 | 12/2002 | Durcan | |
| 6,585,689 B1 * | 7/2003 | Macoviak et al. ....... 604/103.07 |
| 6,613,066 B1 | 9/2003 | Fukaya et al. | |
| 6,988,881 B2 | 1/2006 | Motsenbocker et al. | |
| 7,160,317 B2 | 1/2007 | Mc Hale et al. | |
| 7,407,377 B2 | 8/2008 | Motsenbocker et al. | |
| 2002/0120320 A1 | 8/2002 | Wang et al. | |
| 2002/0163104 A1 | 11/2002 | Motsenbocker et al. | |
| 2003/0130717 A1 | 7/2003 | Hale et al. | |

(Continued)

FOREIGN PATENT DOCUMENTS

EP  0935973  8/1999

*Primary Examiner* — Ryan Severson  
*Assistant Examiner* — Katherine M Shi  
(74) *Attorney, Agent, or Firm* — Vidas, Arrett & Steinkraus, P.A.

(57) ABSTRACT

A stent deployment device is provided with a tapered balloon wrap to protect the edge of a crimped stent during stent deployment. The balloon is wrapped unevenly so that the distal end is looser and has a wider circumference than the proximal end of the balloon. With a stent crimped upon such a balloon, the distal balloon end billows out and covers the distal edge of the stent. This shielding billow prevents the stent edge from becoming damaged or causing harm if the stent is distally impacted while traversing body vessels on the way to the deployment site.

14 Claims, 6 Drawing Sheets

(56) References Cited

U.S. PATENT DOCUMENTS

| | | |
|---|---|---|
| 2003/0163157 A1 | 8/2003 | McMorrow et al. |
| 2003/0187492 A1 | 10/2003 | McHale |
| 2004/0002680 A1* | 1/2004 | Ackerman et al. ......... 604/96.01 |
| 2004/0106973 A1* | 6/2004 | Johnson ....................... 623/1.11 |
| 2004/0215227 A1 | 10/2004 | McMorrow et al. |
| 2005/0059989 A1 | 3/2005 | Eidenschink |
| 2005/0277877 A1 | 12/2005 | Motsenbocker et al. |
| 2007/0112300 A1 | 5/2007 | Roman et al. |
| 2007/0167973 A1* | 7/2007 | Stupecky et al. ............. 606/192 |
| 2008/0119922 A1 | 5/2008 | Alkhatib |

* cited by examiner

EDGE PROTECTION VIA TAPERED BALLOON WRAP

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments, this invention relates to catheter balloons useful in medical dilation and implantation procedures and more particularly to balloons which protect some of the exposed edges of implantable medical devices.

2. Description of the Related Art

Stents, grafts, stent-grafts, vena cava filters, expandable frameworks, and similar implantable medical devices, collectively referred to hereinafter as stents or medical devices, are radially expandable endoprostheses which are typically intravascular implants which are introduced percutaneously when in a smaller introductory configuration and which are then capable of being implanted transluminally and enlarged radially into a deployment configuration. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable). Stents may be implanted to prevent restenosis following angioplasty in the vascular system.

One complication present during stent implantation is outward flaring of the distal edge of the unexpanded stent while being tracked through various body vessels. Thus there is a need for a stent delivery system with improved edge protection.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In at least one embodiment, the invention is directed to a balloon catheter comprising a catheter shaft and an expandable balloon. The expandable balloon has an expanded state and an unexpanded state, a proximal end and a distal end. The expandable balloon is positioned around a distal region of the catheter shaft. The expandable balloon has a length, and is defined by a proximal end, a distal end, and a working portion extending therebetween. In the unexpanded state, the expandable balloon comprises a collapsed portion disposed about the catheter shaft and at least one wing extending from the collapsed portion. The wing has a wrapped state and an unwrapped state, in the wrapped state the wing is wrapped about the collapsed portion. The wing in the wrapped state provides a surface of the balloon which extends further outward in a radial direction from the catheter shaft at the distal end of the balloon than at the proximal end of the balloon.

The invention is also directed to a method of deploying a medical device comprising the steps of providing a medical device crimped about a balloon catheter, the balloon catheter having a catheter shaft and an expandable balloon. The expandable balloon has an expanded state and an unexpanded state, a proximal end and a distal end. The expandable balloon is positioned around a distal region of the catheter shaft. The expandable balloon has a length. The balloon is defined by a proximal end, a distal end, and a working portion extending therebetween. In the unexpanded state, the expandable balloon comprises a collapsed portion disposed about the catheter shaft and at least one wing extending from the collapsed portion, the wing wrapped about the collapsed portion. The wing is more tightly wrapped about the collapsed portion at the distal end of the balloon than at the proximal end of the balloon. The method also comprises the steps of positioning the medical device at a position in a patient's body; and inflating the expandable balloon.

The invention is also directed to a balloon catheter comprising a catheter shaft and an expandable balloon. The expandable balloon has an expanded state and an unexpanded state, a proximal end and a distal end. The expandable balloon is positioned around a distal region of the catheter shaft. The expandable balloon has a length. The balloon is defined by a proximal end, a distal end, and a working portion extending therebetween. In the unexpanded state the expandable balloon comprises a collapsed portion disposed about the catheter shaft and at least one wing extending from the collapsed portion, the wing wrapped about the collapsed portion. The wing bulges radially outward from catheter shaft at the distal end of the balloon as compared to the proximal end of the balloon.

This and other aspects of the invention are described in more detail in the accompanying description and drawings.

BRIEF DESCRIPTION OF THE SEVERAL VIEWS OF THE DRAWINGS

The invention is best understood from the following detailed description when read in connection with accompanying drawings, in which.

DETAILED DESCRIPTION OF THE INVENTION

Figure 1:
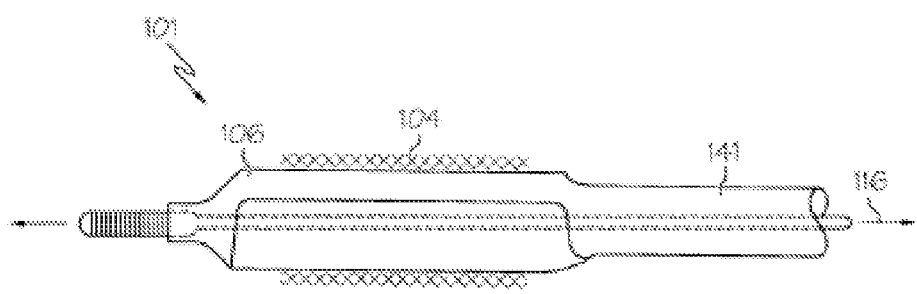
FIG. 1 is side view of a PRIOR ART balloon wrapped around a deployment catheter with a device crimped about the balloon.

The invention will next be illustrated with reference to the figures wherein the same numbers indicate similar elements in all figures. Such figures are intended to be illustrative rather than limiting and are included herewith to facilitate the explanation of the apparatus of the present invention. For the purposes of this disclosure, like reference numerals in the figures shall refer to like features unless otherwise indicated. Depicted in the figures are various aspects of the invention. Elements depicted in one figure may be combined with, or substituted for, elements depicted in another figure as desired.

Referring now to FIG. 1, there is shown a PRIOR ART apparatus (101) in the introductory configuration (the unexpanded state) which is used for the deployment of medical devices (104) including stents, sheaths, grafts, stent-grafts, vena cava filters, expandable prosthesis and the like, and any combination thereof. The apparatus (101) comprises a catheter (141) and an inflation balloon (106). The balloon (106) is wrapped around the catheter (141) in an even manner along its longitudinal axis (116).

Figure 2A:
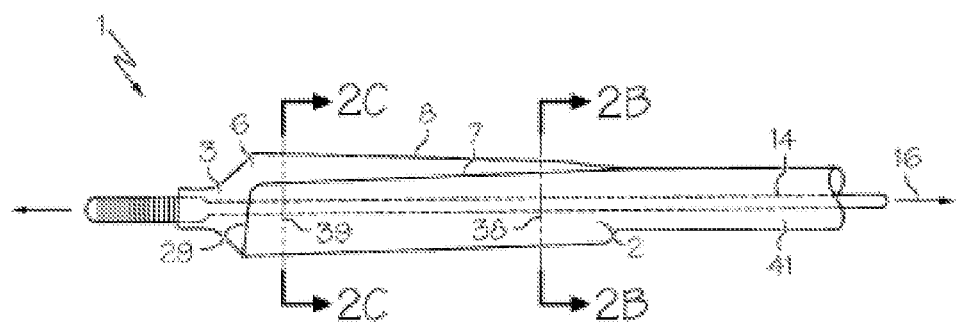
FIG. 2A is a lateral view of a balloon wrapped around a deployment catheter. The balloon is more tightly wrapped at the proximal end than at the distal end.
Figure 2B:
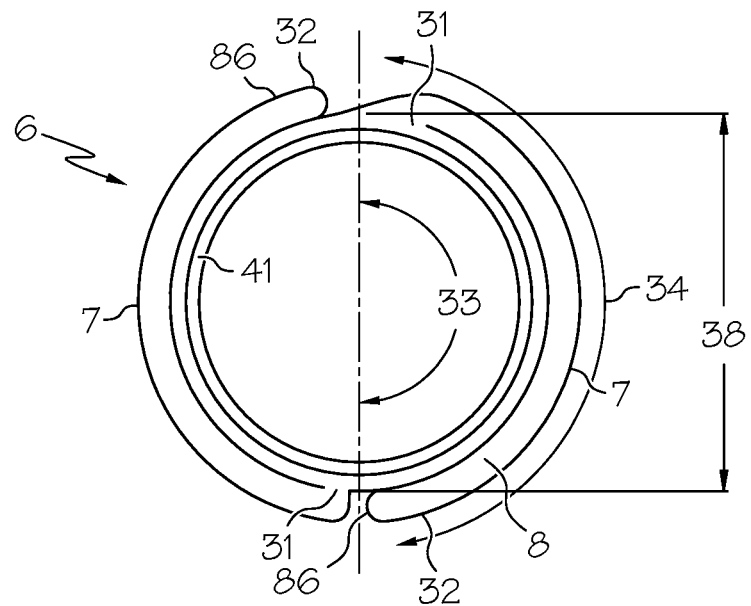
FIG. 2B is a cross section taken along line 2B-2B of FIG. 2A showing a portion of a wing having a smaller arc length and a larger diameter.
Figure 2C:
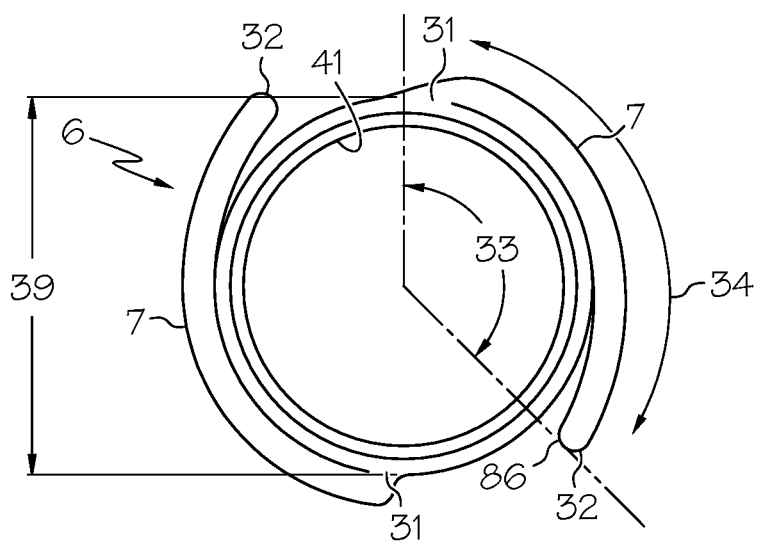
FIG. 2C is a cross section taken along line 2C-2C of FIG. 2A showing a portion of a wing having a larger arc length and a smaller diameter.
Figure 5:
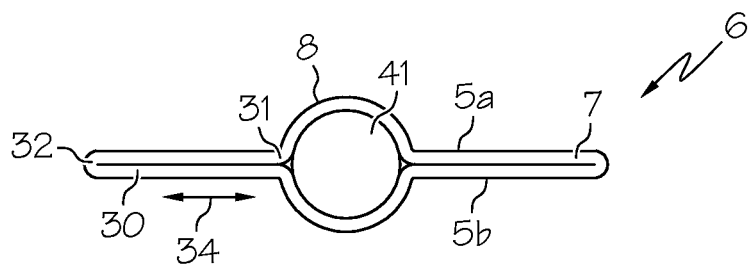
FIG. 5 is a cross sectional view of a deflated balloon around a catheter. The balloon has a collapsed region and two wings.

FIG. 2A shows an embodiment of the invention in which an apparatus in the unexpanded state has a deflated balloon (6) which is wrapped around the catheter (41). The balloon (6) has a length along which a longitudinal axis (16) spans. At least some of the balloon (6) in its unexpanded state is in the form of one or more wings (7) having a wingspan, a wrapped state and an unwrapped state. FIG. 5 illustrates a cross-sectional view of the unwrapped state. FIG. 2A shows that in the wrapped state one or more wings (7) is folded over a collapsed portion of the balloon (6). FIGS. 2B and 2C illustrate that the wingspan (34) is the length of balloon material extending between the wing base (31) where the wing abuts the collapsed portion (8) and the edge (86) of the wing. The wingspan is measured along the wing in a direction perpendicular to the longitudinal axis of the balloon. The wingspan may be a constant length everywhere along the wing or it may be of a variable length, depending on the shape of the wing.

In FIG. 2A, the balloon has two wings which wrap about the collapsed portion of the balloon and the catheter to differing extents along the length of the wing. As shown in FIGS. 2A-2C, the portion of the wing at the proximal end (2) of the balloon wraps about the collapsed portion of the balloon and catheter to a greater extent than the portion of the wing at the distal end (29) of the balloon. Thus, the wrapped portion of the wing subtends arcs of different degree depending upon where the arc is measured along the length of the wing. The proximal end of the wing subtends a greater arc than does the distal end of the wing. The arc is measured based on an angle defined by a first line extending radially outward from the longitudinal axis of the balloon and through the wing base and a second line extending radially outward from the longitudinal axis of the balloon and through the wing tip.

For the purposes of this application, an arc can subtend 360 degrees or more if the wing extend one or more revolutions about the collapsed portion of the balloon. FIGS. 2B and 2C illustrate cross sections of FIG. 2A where the wings subtend different arcs. FIG. 2B is a more proximal portion of the balloon and FIG. 2C is a more distal portion of the balloon.

In at least one embodiment, wing (7) provides a surface of the balloon (6) which extends further outward in a radial direction from the catheter shaft (41) at the distal end of the balloon than at the proximal end of the balloon, as shown in FIG. 2A. In at least one embodiment, the wing (7) bulges radially outward from the catheter shaft at the distal end of the balloon (6) as compared to the proximal end of the balloon (6).

In FIG. 2C the more loosely wrapped distal portion of the balloon subtends a lesser arc as compared with the arc of FIG. 2B. Wing (7) of FIG. 2C does not extend as much around the collapsed portion (8) and instead has a longer diameter (39). In contrast FIG. 2B shows that the more tightly wrapped wing (7) of the more proximal section of the balloon subtends a greater angle and does not extend as far in a radially outward direction, as the wing in a distal section of the balloon. In both FIG. 2B and 2C, the distance between the wing base (31) and the edge (86) are equal. The different folding arrangement allows for the formation of a bulge in balloon material which can shield the distal edge of the device from impacting or snagging the body vessels it is tracked through. In at least one embodiment, the angles subtended by the arcs (33) progressively increase according to a particular pattern between the longer distal diameter (39) and the shorter proximal diameter (38). In at least one embodiment, the differences in arcs (33) are a result of different amounts of torque applied to different portions of the balloon when it is wrapped around the catheter (41). The most distal end (29) of the balloon wing (7) is wrapped with a considerably less amount of torque than the proximal end (2). FIG. 2C also illustrates an embodiment in which the distal end of at least one wing (7) is wrapped such that it spirals along a clockwise path relative to a distal perspective of the catheter shaft (41). In at least one embodiment illustrated in FIGS. 6 and 7, the distal end of at least one wing (7) spirals along a counterclockwise path relative to a distal perspective of the catheter shaft (41).

Figure 3:
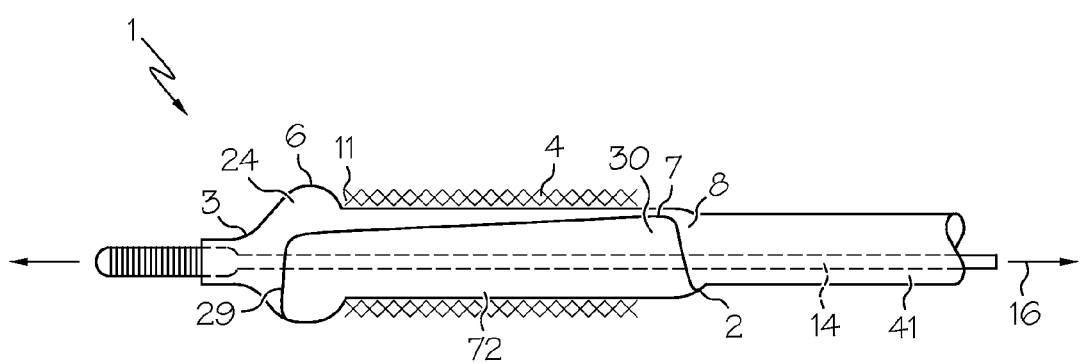
FIG. 3 is a lateral view of a medical device crimped about a balloon which is wrapped around a core member, the balloon is more tightly wrapped at the proximal end than at the distal end.

FIG. 3 illustrates a balloon (6) with a wing (7) having a proximal end (30) characterized by an arc which subtends a greater angle than that of the distal end (29) of the wing with a device (4) crimped about the balloon (6). The portion of the balloon (6) between the proximal and distal ends is the working portion (72). In at least one embodiment, a medical device (4) is crimped about at least a portion of the working portion (72). The crimped device (4) remains in place while the apparatus (1) is in its introductory configuration (unexpanded state). Once the apparatus (1) positions the device (4) at the deployment site, the balloon (6) is filled with fluid and inflates to assume its deployment configuration (expanded state) thereby expanding and deploying the device (4).

In at least one embodiment, the apparatus (1) has a shielding bulge (24) to protect the distal end (11) of the device (4). The shielding bulge (24) is useful to protect the distal edge (11) of the device from protuberances projecting from the body vessels the apparatus (1) travels through. If left unshielded the protruding edge (11) of the device (4) can possibly become entangled or ensnarled with such body vessels that it encounters. In addition, because the path the device (4) travels through the body vessels is not linear, the device (4) may flex and bend as it travels along a curved path and such bending and flexing may result in the device's distal end (11) flaring radially away from the balloon (6) surface further increasing the likelihood of entanglement or becoming ensnarled.

In at least one embodiment, the differential in wrapping the wing(s) (7) enhances the shielding bulge (24). At the distal end (3) of the balloon, the wing (7) is less tightly wrapped (subtends a lesser arc) and billows out from under the device (4) to form a shielding bulge (24). The more tightly wrapped proximal end (2) (where the wing subtends a greater angle) in contrast is more streamlined. The different wrappings cause the balloon material to compress in a distal direction by the crimped device (11). This in turn causes the balloon material at the shielding bulge (24) to curve up from under the device more steeply and extend more radially than would occur in the absence of the differential. As a result, the differential causes a greater bulge (24) to form from a wing (7) of uniform wingspan along its length than would otherwise occur in a wing (7) having no difference in wrapping. This allows for better coverage of the distal end (11) of the device (4) with less balloon material.

Figure 2D:
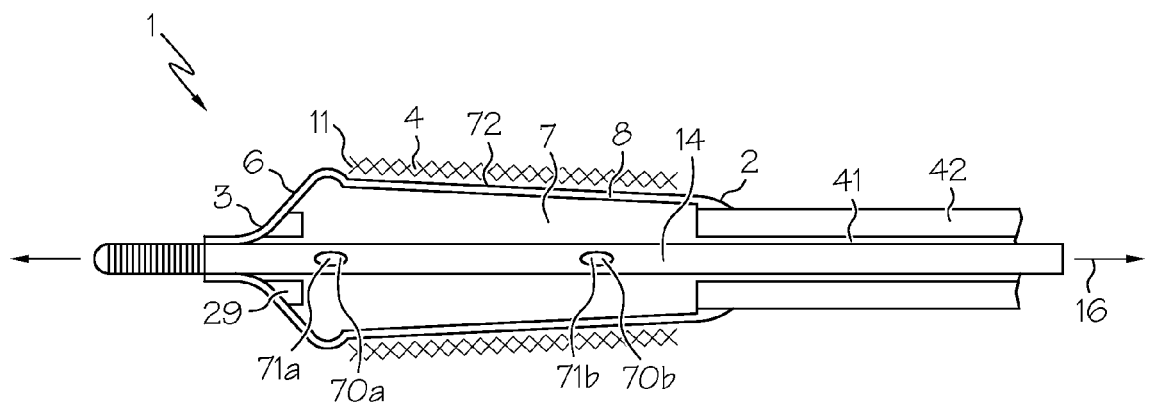
FIG. 2D is a lateral cross-sectional view of a medical device crimped to a balloon wrapped around a deployment catheter. The balloon is more tightly wrapped at the proximal end than at the distal end.

As the apparatus (1) tracks distally through body vessels, potential impacts between the distal end (11) of the device (4) and a body vessel wall are blocked by this shielding bulge (24), preventing deformation of the device (4). In at least one embodiment, the most distal portion (11) of the medical device (4) is formed out of a column or annular element shaped in an undulating pattern with alternating peaks and troughs. An example of such a medical device is a stent such as that shown in U.S. Pat. No. 6,348,065. The shielding bulge (24) prevents the peaks and troughs from becoming hooked or snagged on any protrusions extending from body vessels the apparatus traverses. In at least one embodiment as shown in FIG. 3, the device (4) retains a generally cylindrical shape of generally uniform diameter when crimped on the balloon (6). As shown in FIG. 2D, in at least one embodiment the device (4) is tapered when crimped on the balloon. The crimping of the device on the balloon may increase or decrease the tapered shape of the balloon (6).

Figure 8:
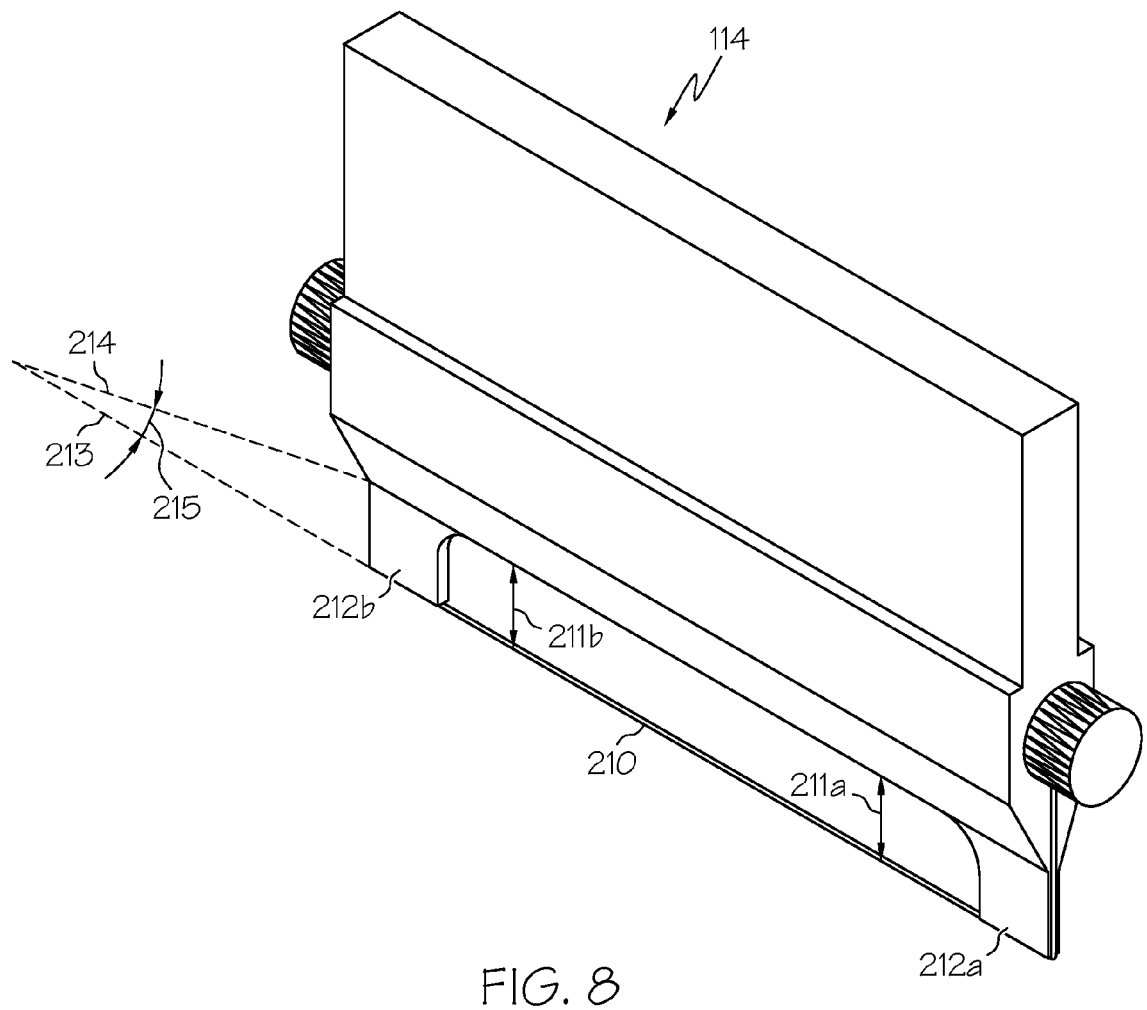
FIG. 8 is a perspective view of an impinging member for folding the balloon more tightly at the proximal end than at the distal end.
Figure 9:
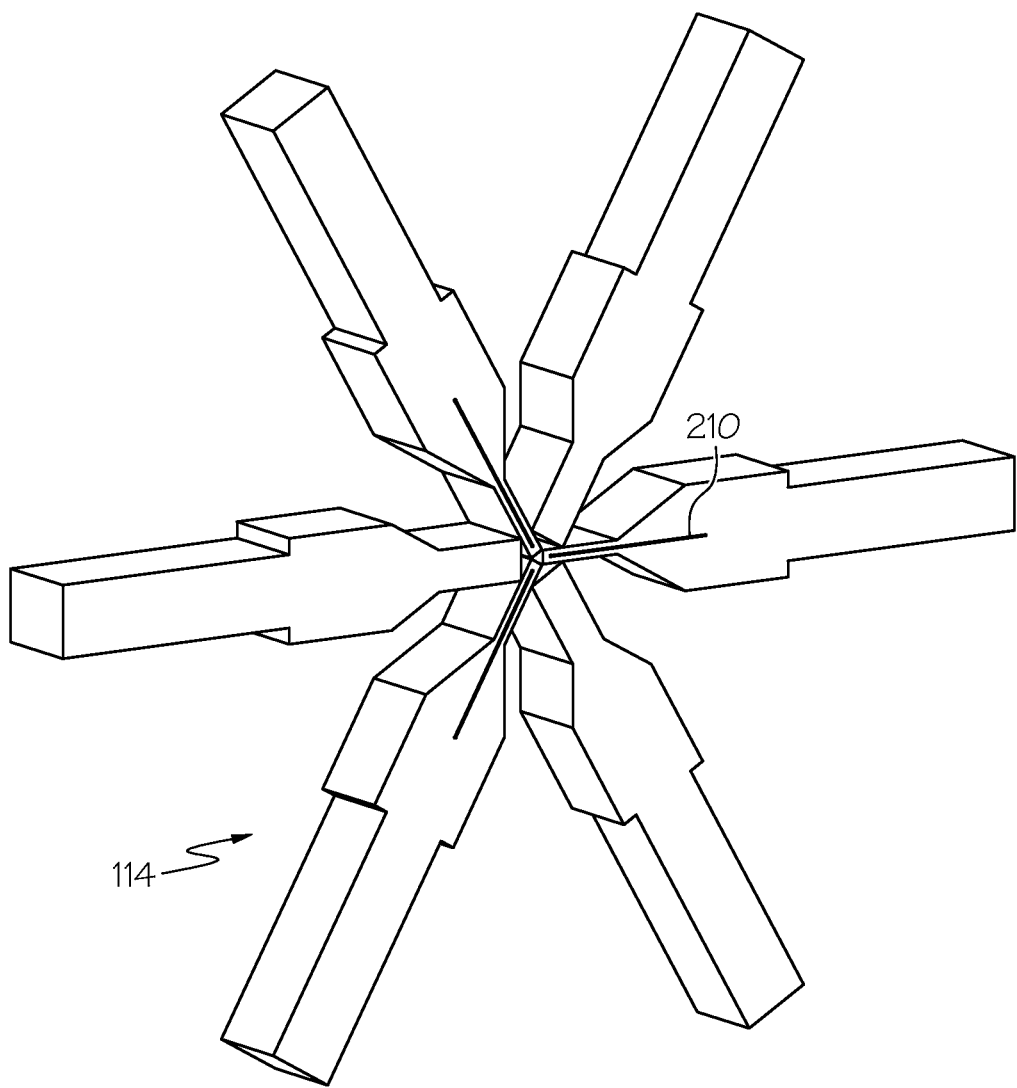
FIG. 9 is a perspective view of one or more impinging members folding a balloon more tightly at the proximal end than at the distal end.

Referring now to FIGS. 8 and 9 there is shown an apparatus for folding the balloon to form a shielding bulge. In at least one embodiment, the apparatus described in US published application 2003/0163157 A1 (the entire contents of which are hereby incorporated by reference) is used to fold the balloon wings to form a shielding bulge. In at least one embodiment as shown in FIG. 8, the apparatus utilizes an adapted impinging member (114) having a line or blade (210) extending between blade holders (212a, 212b) of different lengths (211a, 211b). The length difference between the longer blade holder (211a) and the shorter blade holder (211b) causes the blade (210) to extend along an axis (213) which is at a non-zero angle (215) relative to the axis (214) of the impinging member (114) as a whole. When the blade (210) presses the balloon material, the angled blade causes balloon material nearer to the longer blade holder (212a) to be displaced more, and causes balloon material closer to the shorter blade holder (212b) to be displaced less. During at least some operations of the folding process, the wing portions which are subject to greater displacement wind further and more tightly about the balloon more tightly than those portions of the wing which are subject to lesser displacements.

The angle of the blade may be selected so that the blade applies a gradually increasing degree of displacement from the proximal end to the distal end of a wing, proportional to the difference in fold tightness desired in the folded balloon. FIG. 9 shows a number of such adapted impinging members (114) positioned together in the configuration they would assume when cooperatively folding a balloon.

Figure 4:
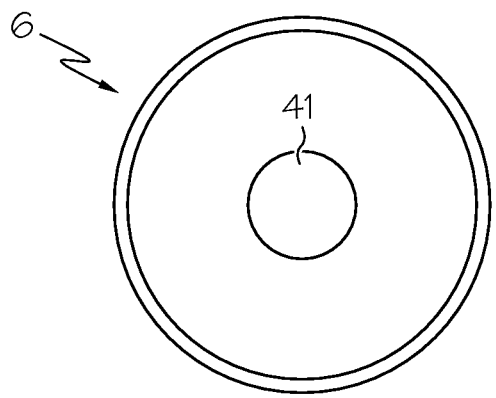
FIG. 4 is a cross sectional view of an inflated balloon around a catheter.
Figure 6:
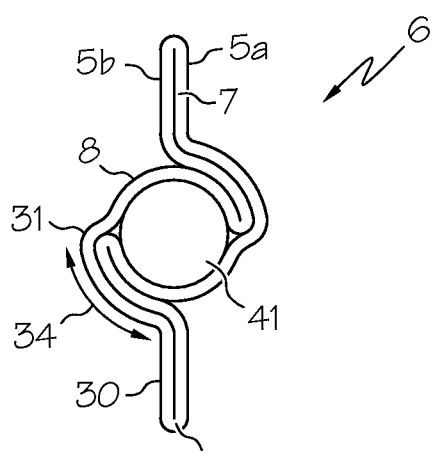
FIG. 6 is a cross sectional view of a deflated balloon around a catheter. The balloon has two wings which are partially wrapped around a collapsed region.
Figure 7:
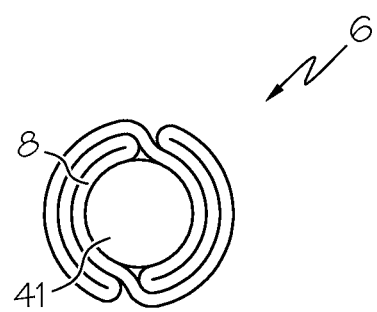
FIG. 7 is a cross sectional view of a deflated balloon around a catheter. The balloon has two wings which are completely wrapped around a collapsed region.

Referring now to FIGS. 4-7 there are shown steps in a method of constructing the apparatus (1). In a first step, as shown in FIG. 4, a balloon (6) is sealingly engaged to catheter (41) and is inflated to an expanded state by the introduction of fluid. FIGS. 5 and 6 show the deflated balloon (6) with wings (7) which extend from a wing base (31) adjacent to the collapsed portion (8) to the wingtip (32). The wings (7) each have two sides (5a, 5b) which when deflated abut each other. The collapsed portion (8) is that portion of the balloon (6) which upon deflation surrounds the catheter (41) and may be positioned in direct contact with the catheter. FIGS. 6 and 7 shows the wings (7) of the deflated balloon (6) wrapped around the collapsed portion (8) to form a folded configuration. In the pleated configuration, the balloon wings (7) are positioned against the collapsed portions (8). Other devices such as those utilizing pleating elements as described in published US application 2002/0163104A1 and U.S. Pat. Nos. 5,053,007, 5,147,302, and 5,342,307 all of which are hereby incorporated by reference in their entirety can also be used as according to the following modifications to fold the inventive balloon configuration.

A pleating device comprising one or more serially positioned pleating elements is positioned along the balloon's length. Each pleating element is positioned adjacent to and grasps a particular region of the wing along the length of the wing and folds that region about the collapsed portion. The proximal most pleating element wraps the proximal most region of the wing to form the tightest arc about the collapsed portion of the balloon by applying more pleating torque to the proximal most region of the wing than any other element applies to any other region. The distal most pleating element wraps the distal most region of the wing to form the loosest arc about the collapsed portion by applying less pleating torque to the distal most region of the wing than to any other region. Contemplated embodiments include balloons in which the region having the loosest arc is not the most distal region of the wing and in which the region having the tightest arc is not the most proximal region of the wing.

In at least one embodiment, the pleating device utilizes one pleating element on more than one of the regions of a wing (7). In this embodiment, the pleating element first grasps a portion of the wing and pleats it with a given amount of pleating torque, and then increases or decreases the amount of pleating torque as it moves along the wing in a distal or proximal direction.

In at least one embodiment, the torque of the pleating force causes the wings to form arcs of decreasing angular extent from the distal (3) to the proximal (2) ends according to a linearly proportional amount resulting in a more loosely wrapped distal end (3) than proximal end (2). In at least one embodiment, the balloon is wrapped so as to have a generally linear taper in the extent to which the balloon bulges radially outward. In at least one embodiment, the torque of the pleating force holding the regions in their particular arcs decreases exponentially from the distal (3) to the proximal (2) ends resulting in a much more loosely wrapped distal end (3) than proximal end (2) and a generally arced taper extending along the wrapped balloon (6). A tapered unexpanded device can be crimped over this tapering balloon (6).

In at least one embodiment, the pleating force applied to one or more regions of the wing will include a longitudinal component. Typically, a tighter arc will be achieved where less longitudinal force is applied and a wider arc will be achieved where more longitudinal force is applied.

FIG. 2D illustrates at least one embodiment of a catheter (41) having an uneven folded wing configuration further comprising one or more ports (70a, 70b). The catheter (41) has an outer tubular member (42) through which a portion of an inner tubular member (14) extends. The inflation balloon (6) is sealingly engaged at its distal end (29) to a portion of the catheter (41) and at its proximal end (2) to the outer tubular member (42). In at least one embodiment the distal end (29) of the balloon (6) is engaged to the inner tubular member (14). The space between the inner tubular member (14) and the outer tubular member (42) is the inflation lumen which is in fluid communication with the balloon (6). In at least one embodiment, fluid is introduced to the inflation lumen of the balloon (6) through the one or more ports (70a, 70b) in the inner tubular member (14). Other methods of introducing fluid into the balloon are also known in the art.

In some embodiments, the proximal end of the balloon may be sealingly engaged to the inner tubular member and the distal end of the balloon may be sealingly engaged to the outer tubular member.

In some embodiments, the catheter is constructed and arranged to apply a greater amount of inflating force at the distal end (3) than at the proximal end (2). This inflation characteristic, in combination with the more loosely wrapped folds at the distal end (3), results in an apparatus (1) which provides significantly more expansion force to the device at the distal end (3) than at the proximal end (2). Such a design is useful when the protocol calls for a device which may be more rigid at its distal end than at its proximal end. In at least one embodiment, the only port from which fluid flows into the balloon (6) is located at or near the distal end of the balloon. In at least one embodiment, there are at least two ports (70a, 70b), having independent sources of fluid, the proximal port (70b) having a greater amount of fluidic flux when inflating the balloon (6). In at least one embodiment, there are at least two ports (70a, 70b) which are fed fluid from a common source, the more distal port (70a) has a larger sized aperture (71a) than the aperture (71b) of the more proximal port (70b) and provides a greater amount of fluidic flux when inflating the balloon.

In at least one embodiment, when the balloon is inflated, a greater amount of inflating force is applied at or near the proximal end (2) than at the distal end (3) of the balloon. This at least partially compensates for the greater amount of force needed to unfold the tightly wound proximal end (2) relative to the loosely wound distal end (3) and facilitates a more even inflation of the balloon (6) and a more consistent expansion of the device. In at least one embodiment, the only port from which fluid flows into the balloon (6) is located at or near the proximal end (2) of the balloon. In at least one embodiment, there are at least two ports, having independent sources of fluid, the distal port having a greater amount of fluidic flux when inflating the balloon. In at least one embodiment, there are at least two ports which are fed fluid from a common source, the more distal port has a larger sized aperture than the more proximal port and provides a greater amount of fluidic flux when inflating the balloon.

At least one embodiment of the invention is directed to a balloon catheter comprising a catheter shaft and an expandable balloon. The expandable balloon has an expanded state and an unexpanded state, a proximal end and a distal end. The expandable balloon is positioned around a distal region of the catheter shaft. The expandable balloon has a length, the length being defined by a proximal end, a distal end, and a working portion extending therebetween. In the unexpanded state: the expandable balloon comprises a collapsed portion disposed about the catheter shaft, at least one wing extending from the collapsed portion, and the wing is non-uniformly wrapped about the catheter shaft and/or about the collapsed portion.

At least one embodiment of the invention is directed to a balloon catheter comprising a catheter shaft and an expandable balloon. The expandable balloon has an expanded state and an unexpanded state, a proximal end and a distal end. The expandable balloon is positioned around a distal region of the catheter shaft. The expandable balloon has a length, the length being defined by a proximal end, a distal end, and a working portion extending therebetween. In the unexpanded state: the expandable balloon comprises a collapsed portion disposed about the catheter shaft, at least one wing extending from the collapsed portion, and the wing is wrapped more tightly at the proximal end of the balloon than at the distal end of the balloon.

At least one embodiment of the invention is directed to a balloon catheter comprising a catheter shaft and an expandable balloon. The expandable balloon has an expanded state and an unexpanded state, a proximal end and a distal end. The expandable balloon is positioned around a distal region of the catheter shaft. The expandable balloon has a length, the length being defined by a proximal end, a distal end, and a working portion extending therebetween. In the unexpanded state: the expandable balloon comprises a collapsed portion disposed about the catheter shaft and at least one wing. The balloon catheter further comprises a stent disposed about the balloon. The distal end of the balloon bulges radially outward from the catheter shaft to form a protective layer for a distal-most edge of the stent.

In some embodiments, the device, its delivery apparatus, or other portion of an assembly may include one or more areas, bands, coatings, members, etc. that is (are) detectable by imaging modalities such as X-Ray, MRI, ultrasound, etc. In some embodiments, at least a portion of the device and/or adjacent apparatus is at least partially radiopaque.

In some embodiments at least a portion of the device is configured to include one or more mechanisms for the delivery of a therapeutic agent. Often the agent will be in the form of a coating or other layer (or layers) of material placed on a surface region of the device, which is adapted to be released at the site of the device's implantation or areas adjacent thereto.

The therapeutic agent can be at least one or various types of therapeutic agents including but not limited to: at least one restenosis inhibiting agent that comprises drug, polymer and bio-engineered materials or any combination thereof. In addition, the coating can be a therapeutic agent such as at least one drug, or at least one other pharmaceutical product such as non-genetic agents, genetic agents, cellular material, etc. Some examples of suitable non-genetic therapeutic agents include but are not limited to: at least one anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS) polyethylene oxide, silicone rubber and/or any other suitable substrate. It will be appreciated that other types of coating substances, well known to those skilled in the art, can be applied to the stent (4) as well.

This completes the description of the preferred and alternate embodiments of the invention. The above disclosure is intended to be illustrative and not exhaustive. This description will suggest many variations and alternatives to one of ordinary skill in this art. The various elements shown in the individual figures and described above may be combined, substituted, or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claims below.

The invention claimed is:

1. A balloon catheter comprising:
a catheter shaft and an expandable balloon, the expandable balloon having an expanded state and an unexpanded state, a proximal end and a distal end, the expandable balloon being positioned around a distal region of the catheter shaft, the expandable balloon having a length, and being defined by a proximal end, a distal end, and a working portion extending therebetween, in the unexpanded state the expandable balloon comprising a collapsed portion disposed about the catheter shaft and at least one wing extending from the collapsed portion, the wing having a wrapped state and an unwrapped state, in the wrapped state the wing is wrapped about the collapsed portion,
wherein the wing in the wrapped state provides a surface of the balloon which extends further outward in a radial direction from the catheter shaft at the distal end of the balloon than at the proximal end of the balloon;
the wing in the unwrapped state extending from the collapsed portion along a wing base which extends parallel to the longitudinal axis of the catheter shaft, the wing having an edge which extends from one end of the wing base to the other end of the wing base, wherein in the wrapped state the edge forms a continuous spiral at least part of the way about the longitudinal axis of the catheter shaft, the continuous spiral extending along a majority of the length of the edge; and
the wing in an unwrapped state extending from the collapsed portion along a wing base which extends parallel to the longitudinal axis of the catheter shaft and having a wing tip which extends parallel to the longitudinal axis of the catheter shaft, wherein, in the wrapped state, the wing base extends parallel to the longitudinal axis of the catheter shaft and the wing tip extends non-parallel to the longitudinal axis of the catheter shaft.

2. The balloon catheter of claim 1, the wing having proximal and distal ends, the proximal end of the wing spiraling more tightly about the collapsed portion than the distal end of the wing.

3. The balloon catheter of claim 1, the catheter further comprising an outer tubular member through which at least a portion of an inner tubular member passes, the proximal end of the balloon being sealingly engaged to the outer tubular member, the distal end of the balloon being sealingly engaged to the inner tubular member.

4. The balloon catheter of claim 3, the inner tubular member further comprising a proximal aperture defining an opening in the inner tubular member through which inflating fluid passes into the balloon, the proximal aperture located closer to the proximal end of the balloon than the distal end of the balloon.

5. The balloon catheter of claim 4, the inner tubular member further comprising a distal aperture distal to the proximal aperture, the distal aperture defining an opening in the inner tubular member smaller than the proximal aperture and through which inflating fluid passes into the balloon.

6. The balloon catheter of claim 4, the inner tubular member further comprising a distal aperture defining an opening in the inner tubular member distal to the proximal aperture through which inflating fluid passes into the balloon, the catheter constructed and arranged to pass fluid into the balloon with greater flux at the proximal aperture than at the distal aperture.

7. The balloon catheter of claim 1, the proximal and distal ends of the balloon having circumferences, the circumference of the distal end of the balloon being greater than the circumference of the proximal end of the balloon.

8. The balloon catheter of claim 1 wherein a distal end of the wing spirals along a clockwise path relative to a distal perspective of the catheter shaft.

9. The balloon catheter of claim 1, wherein a distal end of the wing spirals along a counterclockwise path relative to a distal perspective of the catheter shaft.

10. The balloon catheter of claim 1 further comprising a medical device, wherein in the unexpanded state the medical device is crimped over and around the balloon, in the expanded state the medical device is enlarged and deployed, the medical device selected from the group consisting of stents, grafts, stent-grafts, vena cava filters, expandable frameworks, and any combination thereof.

11. The balloon catheter of claim 10 in which in the unexpanded configuration at least some of the distal end of the balloon billows out from under the distal edge of the medical device to form a shielding bulge which shields the distal edge of the medical device.

12. The balloon catheter of claim 11 in which at least the most distal portion of the medical device is formed in an undulating pattern.

13. A balloon catheter comprising:
a catheter shaft and an expandable balloon,
the expandable balloon having an expanded state and an unexpanded state, a proximal end and a distal end, the expandable balloon being positioned around a distal region of the catheter shaft, the expandable balloon having a length, the balloon being defined by a proximal end, a distal end, and a working portion extending therebetween, in the unexpanded state the expandable balloon comprising a collapsed portion disposed about the catheter shaft and at least one wing extending from the collapsed portion, the wing wrapped about the collapsed portion the wing having a bulge which extends radially outward from the catheter shaft, the balloon continuously tapering over the majority of the length of the balloon; and the wing has a base and a width, the base extending parallel to a longitudinal axis of the catheter shaft, the width of the wing defined by a distance along the wing between an edge and the wing base, wherein the width continuously increases from one end of the wing base to the other end of the wing base.

14. A balloon catheter comprising:

a catheter shaft and an expandable balloon, the expandable balloon having an expanded state and an unexpanded state, a proximal end and a distal end, the expandable balloon being positioned around a distal region of the catheter shaft, the expandable balloon having a length, the balloon being defined by a proximal end, a distal end, and a working portion extending therebetween, in the unexpanded state the expandable balloon comprising a collapsed portion disposed about the catheter shaft and at least one wing extending from the collapsed portion, the wing wrapped about the collapsed portion the wing having a bulge which extends radially outward from the catheter shaft, the balloon continuously tapering over the majority of the length of the balloon; and the wing has a base and a width, the base extending parallel to a longitudinal axis of the catheter shaft, the width as measured along the wing from an edge of the wing to the collapsed portion, wherein the width continuously increases from one end of the wing base to the other end of the wing base.

\* \* \* \* \*